United States Patent
Kitamura

(10) Patent No.: US 9,156,773 B2
(45) Date of Patent: Oct. 13, 2015

(54) ALICYCLIC DICARBOXYLIC ACID ESTER COMPOUND AND MANUFACTURING METHOD THEREOF

(71) Applicant: Mitsubishi Gas Chemical Company, Inc., Chiyoda-ku (JP)

(72) Inventor: Mitsuharu Kitamura, Kurashiki (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 14/431,442

(22) PCT Filed: Oct. 11, 2013

(86) PCT No.: PCT/JP2013/077712
§ 371 (c)(1),
(2) Date: Mar. 26, 2015

(87) PCT Pub. No.: WO2014/061571
PCT Pub. Date: Apr. 24, 2014

(65) Prior Publication Data
US 2015/0239823 A1    Aug. 27, 2015

(30) Foreign Application Priority Data

Oct. 15, 2012  (JP) ................................. 2012-227837

(51) Int. Cl.
*C07C 69/75* (2006.01)
*C07C 67/14* (2006.01)
*C07C 51/58* (2006.01)

(52) U.S. Cl.
CPC ................ *C07C 69/75* (2013.01); *C07C 51/58* (2013.01); *C07C 67/14* (2013.01); *C07C 2101/14* (2013.01)

(58) Field of Classification Search
None
See application file for complete search history.

(56) References Cited

U.S. PATENT DOCUMENTS

| | | |
|---|---|---|
| 2,986,584 A | 5/1961 | Sheers et al. |
| 2002/0042496 A1 | 4/2002 | Teranishi et al. |
| 2011/0040030 A1 | 2/2011 | Mijolovic et al. |
| 2012/0238784 A1 | 9/2012 | Kitamura et al. |
| 2013/0123548 A1 | 5/2013 | Muratore et al. |
| 2013/0345477 A1 | 12/2013 | Kitamura et al. |
| 2014/0087990 A1 | 3/2014 | Kitamura |

FOREIGN PATENT DOCUMENTS

| | | |
|---|---|---|
| JP | 2000 290356 | 10/2000 |
| JP | 2004 124022 | 4/2004 |
| JP | 2005 298555 | 10/2005 |
| JP | 3862538 | 12/2006 |
| JP | 2009 149577 | 7/2009 |
| JP | 2011 521038 | 7/2011 |
| JP | 2012 140354 | 7/2012 |
| WO | 2007 110978 | 10/2007 |
| WO | 2011 002044 | 1/2011 |
| WO | 2011 138747 | 11/2011 |
| WO | 2012 133189 | 10/2012 |

OTHER PUBLICATIONS

International Search Report Issued Dec. 10, 2013 in PCT/JP13/077712 Filed Oct. 11, 2013.

*Primary Examiner* — Yevegeny Valenrod
(74) *Attorney, Agent, or Firm* — Oblon, McClelland, Maier & Neustadt, L.L.P.

(57) ABSTRACT

The alicyclic dicarboxylic acid ester compound of the present invention is represented by the following formula (1):

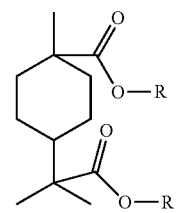

(1)

wherein R each independently represent an alkyl group having 1 to 4 carbon atoms.

3 Claims, 14 Drawing Sheets

ALICYCLIC DICARBOXYLIC ACID ESTER COMPOUND AND MANUFACTURING METHOD THEREOF

TECHNICAL FIELD

The present invention relates to a new alicyclic dicarboxylic acid ester compound having a cyclohexane ring, and a manufacturing method thereof.

BACKGROUND ART

A polyester resin synthesized from an alicyclic dicarboxylic acid and an alicyclic diol can be applied to use as optical materials, electronic information materials, and medical appliance materials, due to excellence in transparency, heat resistance, weather resistance, gas barrier property, and optical properties.

For example, using 1,4-cyclohexane dicarboxylic acid (1,4-CHDA) as alicyclic dicarboxylic acid, and 1,4-cyclohexane dimethanol (1,4-CHDM) as alicyclic diol, a polyester resin excellent in biodegradability (refer to, for example, Patent Document 1), a conductive polyester emitting a less amount of gas (refer to, for example, Patent Document 2), and a polyester having a short foam-disappearing time, suitable for use in medical application (refer to, for example, Patent Document 3) are synthesized. Furthermore, using tricyclo[3.3.1.1$^{3,7}$]decane dicarboxylic acid as alicyclic dicarboxylic acid, and tricyclo[3.3.1.1$^{3,7}$]decane diol as alicyclic diol, a polyester resin having small optical anisotropy, excellent in moldability, is synthesized (refer to, for example, Patent Document 4).

LIST OF PRIOR ART DOCUMENTS

Patent Document

Patent Document 1
  Japanese Patent Laid-Open No. 2000-290356
Patent Document 2
  Japanese Patent Laid-Open No. 2004-124022
Patent Document 3
  Japanese Patent Laid-Open No. 2005-298555
Patent Document 4
  Japanese Patent No. 3862538

SUMMARY OF INVENTION

Problems to be Solved by Invention

An object of the present invention is to provide a new alicyclic dicarboxylic acid ester compound having a cyclohexane ring and a manufacturing method thereof.

Means for Solving Problems

The present inventor has investigated a method of manufacturing a new alicyclic dicarboxylic acid ester compound represented by the following formula (1) from 4-isopropenyl-1-methyl-1-cyclohexene represented by the following formula (3), and found out that the new alicyclic dicarboxylic acid ester compound represented by the following formula (1) can be manufactured by, for example, reacting 4-isopropenyl-1-methyl-1-cyclohexene represented by the following formula (3) with carbon monoxide in the presence of hydrogen fluoride (hereinafter also referred to as "HF"), subsequently reacting the produced alicyclic dicarboxylic acid fluoride represented by the following formula (2) with alcohol.

The present invention has been thus accomplished based on the finding.

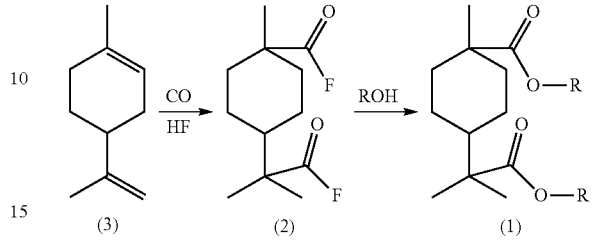

wherein R each independently represent an alkyl group having 1 to 4 carbon atoms.

Specifically, the present invention is described as follows.

[1] An alicyclic dicarboxylic acid ester compound represented by the following formula (1):

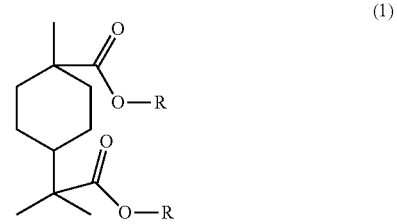

wherein R each independently represent an alkyl group having 1 to 4 carbon atoms.

[2] The alicyclic dicarboxylic acid ester compound according to [1], wherein the compound has a steric structure represented by the following formula (1-1):

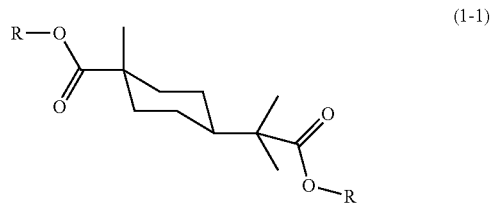

wherein R each independently represent an alkyl group having 1 to 4 carbon atoms.

[3] A method of manufacturing an alicyclic dicarboxylic acid ester compound comprising the steps of:

reacting 4-isopropenyl-1-methyl-1-cyclohexene represented by the following formula (3) with carbon monoxide in the presence of hydrogen fluoride so as to produce an alicyclic dicarboxylic acid fluoride represented by the following formula (2); and reacting the produced alicyclic dicarboxylic acid fluoride represented by the following formula (2) with alcohol so as to produce an alicyclic dicarboxylic acid ester compound represented by the following formula (1):

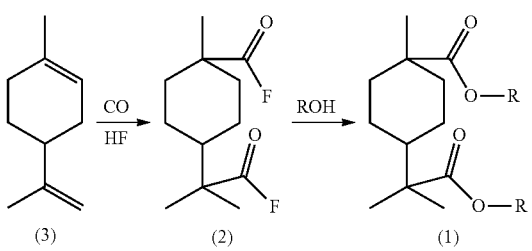

(3)  (2)  (1)

wherein R each independently represent an alkyl group having 1 to 4 carbon atoms.

Advantages of Invention

The new alicyclic dicarboxylic acid ester compound represented by the formula (1) of the present invention can be used, for example, as a raw material of polyester resins. Since the manufacturing method of the present invention uses a compound represented by the formula (3) derived from biomass as a raw material, it can be said that the manufacturing method is environment-friendly in terms of carbon neutrality.

MODE FOR CARRYING OUT INVENTION

Figure 1:
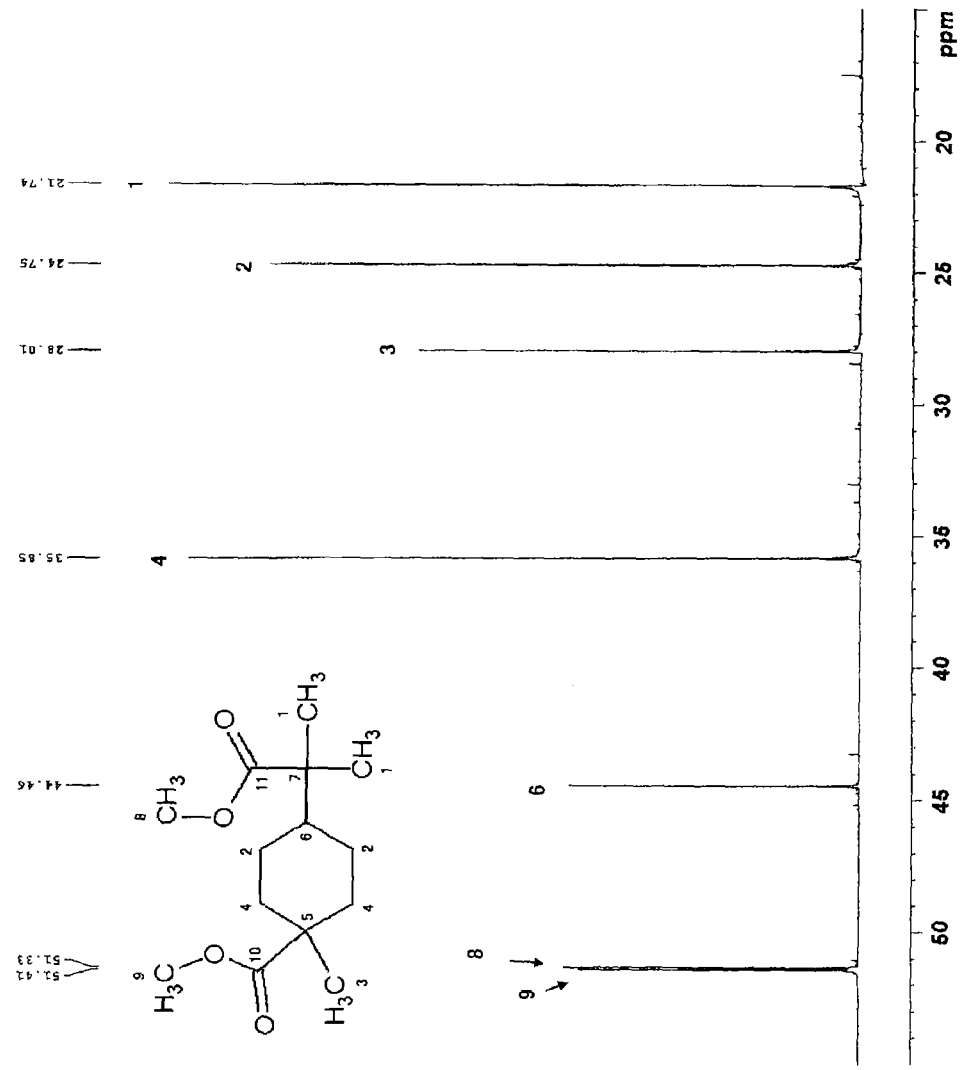
FIG. 1 is a chart showing DEPT 45°-NMR measurement results of a product obtained in Example 1.

The embodiments of the present invention (hereinafter also referred to as "the present embodiment") are described in detail in the following. The following embodiments are, however, provided to illustrate the present invention, and the present invention is not limited thereto only.

The new alicyclic dicarboxylic acid ester compound of the present embodiment is represented by the following formula (1).

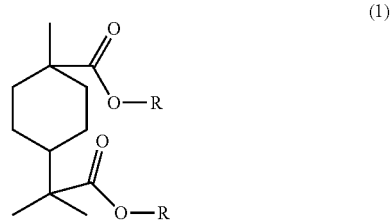

wherein R each independently represent an alkyl group having 1 to 4 carbon atoms.

Examples of the alkyl group represented by R having 1 to 4 carbon atoms in the formula (1) include a methyl group, an ethyl group, an n-propyl group, an isopropyl group, an n-butyl group, an i-butyl group, and a t-butyl group, though not being particularly limited. Among them, a methyl group, an ethyl-group, and an n-propyl group are preferred, a methyl group and an ethyl group are more preferred, and a methyl group is furthermore preferred.

The alicyclic dicarboxylic acid ester compound represented by the formula (1) may be used, for example, as a raw material for polyester resins, and a material excellent in optical properties and heat resistance can be manufactured by using the alicyclic dicarboxylic acid ester compound. Examples of the application of the material having such properties include, but not particularly limited to, optical materials such as lenses.

Due to having a cyclohexane ring, the compound of the present embodiment may have a plurality of steric structures. The steric structure of the compound of the present embodiment is different depending on, for example, whether the functional group or hydrogen atom bonded to the carbon in a cyclohexane ring is at an axial position or an equatorial position, and the steric structure is in a trans or cis configuration due to difference in the position of two functional groups bonded to the carbon in a cyclohexane ring.

The compound of the present embodiment tends to be stabilized, in the case of having a steric structure of a cyclohexane ring with a functional group having a large steric hindrance, such as a 1-methoxy-2-methyl-1-oxopropan-2-yl group, at an equatorial position, and with a hydrogen atom or the like having a small steric hindrance at an axial position. Also, the compound of the present embodiment with a trans configuration tends to have higher reactivity of a reactive substituent such as a carboxylate group. The alicyclic dicarboxylic acid ester compound having such properties is useful as a raw material for a polyester resin excellent in optical anisotropy.

From the viewpoint described above, the compound of the present embodiment is preferably an alicyclic dicarboxylic acid ester compound having a steric structure represented by the following formula (1-1).

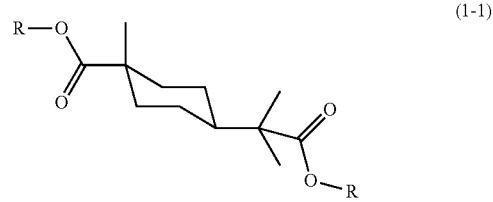

wherein R each independently represent an alkyl group having 1 to 4 carbon atoms.

The method of manufacturing the new alicyclic dicarboxylic acid ester compound of the present embodiment comprises the following steps (a) and (b):

(a) A step of reacting 4-isopropenyl-1-methyl-1-cyclohexene represented by the following formula (3) with carbon monoxide in the presence of hydrogen fluoride (hereinafter also referred to as "HF") so as to produce an alicyclic dicarboxylic acid fluoride represented by the following formula (2)(hereinafter sometimes abbreviated as "carbonylation step"); and (b) A step of reacting the produced alicyclic dicarboxylic acid fluoride represented by the following formula (2) with alcohol so as to produce an alicyclic dicarboxylic acid ester compound represented by the following formula (1) (hereinafter sometimes abbreviated as "esterification step").

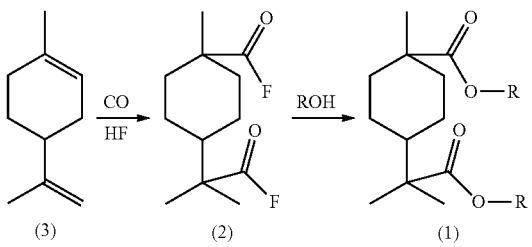

wherein R each independently represent an alkyl group having 1 to 4 carbon atoms.

<(a) Carbonylation Step>

In the step (a), the carbonylation reaction of 4-isopropenyl-1-methyl-1-cyclohexene represented by the following formula (3) is preferably performed in the presence of HF under pressure of carbon monoxide. Through the step (a), an alicyclic carbonyl compound represented by the following formula (2) (hereinafter also referred to as "alicyclic dicarboxylic acid fluoride") is produced. The product of the carbonylation reaction in the step (a) may contain various by-products (containing other isomers).

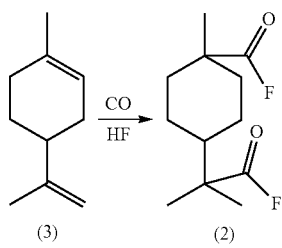

[Carbon Monoxide]

The carbon monoxide for use in the carbonylation step may contain an inert gas such as nitrogen and methane. The carbonylation step is performed under a carbon monoxide partial pressure in the range of preferably 0.5 to 5 MPa, more preferably 1 to 4 MPa, furthermore preferably 1.5 to 3 MPa. Under a carbon monoxide partial pressure of more than 0.5 MPa, the carbonylation reaction proceeds sufficiently without concurrence of side reactions such as disproportionation and polymerization, so that the target substance, i.e. alicyclic dicarboxylic acid fluoride, can be obtained at a high yield. A carbon monoxide partial pressure of 5 MPa or less is preferred, considering the load on equipment.

[Hydrogen Fluoride]

Since HF for use in the carbonylation step functions as a solvent, a catalyst, and a secondary raw material for the reaction, use of substantially anhydrous HF is preferred. In the present embodiment, the substantially anhydrous HF means HF with a water concentration of 200 ppm or less. In the carbonylation step, the amount of HF for use is preferably 4 to 30 times by mole, more preferably 7 to 20 times by mole, furthermore preferably 10 to 15 times by mole, as large as the amount of raw material 4-isopropenyl-1-methyl-1-cyclohexene. With an amount of HF for use of 4 times by mole or more, the carbonylation reaction proceeds efficiently, with concurrence of side reactions such as disproportionation and polymerization being suppressed, so that the target substance, i.e. alicyclic dicarboxylic acid fluoride, can be obtained at a high yield. The amount of HF for use is preferably 30 times by mole or less, more preferably 15 times by mole or less, considering raw material costs and productivity.

[Reaction Conditions]

The type of carbonylation reaction in the step (a) is not particularly limited. Any of a batch type, a semi-continuous type, a continuous type, and the like may be employed.

The reaction temperature of carbonylation reaction in the step (a) is preferably in the range of −50° C. to 30° C., more preferably −40° C. to 0° C., furthermore preferably −30 to −10° C. At a reaction temperature of the carbonylation reaction of 30° C. or less, in particular −10° C. or less, improved selectivity tends to be achieved. The carbonylation reaction in the step (a) is preferably performed at −50° C. or more, considering the reaction rate.

The reaction pressure of carbonylation reaction in the step (a) is preferably in the range of 0.6 to 5.0 MPa, more preferably 1.1 to 4.0 MPa, furthermore preferably 1.6 to 3.0 MPa.

<(b) Esterification Step>

The esterification step is a step of reacting the alicyclic dicarboxylic acid fluoride produced in the carbonylation step with an alcohol having 1 to 4 carbon atoms so as to produce an alicyclic dicarboxylic acid ester compound. In the esterification step, the reaction liquid produced in the carbonylation step may be directly used. Considering the corrosivity of a reaction apparatus, in the esterification step, a method in which a predetermined amount of alcohol is added to the reaction liquid produced in the carbonylation step is preferred. Alternatively, an excessive amount of HF may be distilled away from the reaction liquid produced in the carbonylation step and then alcohol may be added to the reaction liquid for esterification.

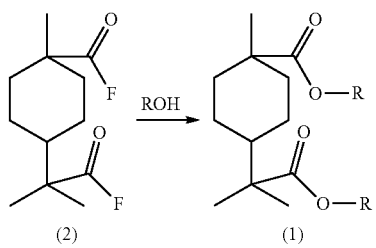

wherein R each independently represent an alkyl group having 1 to 4 carbon atoms.

Specific examples of the alcohol for use in the esterification step include methanol, ethanol, n-propanol, isopropanol, n-butyl alcohol, isobutyl alcohol, and tert-butyl alcohol, though not being particularly limited. Among them, methanol or ethanol is preferred, considering the reactivity. In the esterification step, one type of alcohol may be used alone or two or more types may be used in combination.

The amount of alcohol for use in the esterification step is preferably 1.0 to 2.5 times by mole, more preferably 1.2 to 2.3 times by mole, furthermore preferably 1.5 to 2.0 times by mole, as large as the amount of raw material 4-isopropenyl-1-methyl-1-cyclohexene in the carbonylation step. With an amount of alcohol for use of 1.0 times by mole or more, the remaining amount of unreacted alicyclic dicarboxylic acid fluoride is small, resulting in little corrosion of apparatus in a subsequent step, which is preferable. An amount of alcohol for use of 2.5 times by mole or less is preferred, from the viewpoint of suppressing the corrosion of apparatus by water produced in an intermolecular dehydration reaction of alcohol.

The reaction temperature in the esterification step is preferably −40° C. or more and 20° C. or less, more preferably −35 to 10° C., furthermore preferably −30 to 0° C., from the viewpoint of suppressing decomposition of the alicyclic dicarboxylic acid ester compound represented by the above formula (1). With a reaction temperature of −40° C. or more, the esterification rate can be accelerated to improve the yield. With a reaction temperature of 20° C. or less, the decomposition of ester can be suppressed and by-product water due to dehydration reaction of alcohol can be suppressed.

The esterification step is preferably performed under normal pressure.

<Other Steps>

The manufacturing method of the present embodiment may comprise other steps other than the steps (a) and (b) described above. Examples of the other step include a liquid-liquid extraction step, a catalyst recovery step, a neutralization and washing step, an auxiliary agent recovery step, and a refining step, though not being particularly limited.

Examples of the refining step include a step of, after distilling HF away from the reaction liquid containing an alicyclic dicarboxylic acid ester compound represented by the formula (1) produced in the esterification step, refining the reaction liquid by a conventional method such as distillation, though not being particularly limited.

EXAMPLES

Hereinafter, the present invention will be specifically described with reference to Examples, but the present invention is not intended to be limited to these examples. Unless otherwise specified, "%" in the following means mass %.

<Analytical Method and Conditions>

[Gas Chromatography]

In gas chromatography, a measurement apparatus GC-17A made by SHIMADZU CORPORATION and a capillary column HR-1 made by ULBON (0.32 mmφ×25 m×0.50 μm) were used. The temperature-rising conditions were set such that the temperature was raised from 100° C. to 300° C. at a rate of 5° C./min.

[Yield and Isomer Ratio of Dicarboxylic Acid Ester Compound]

By gas chromatography analysis, the area ratios (GC %) of several types of isomeric dicarboxylic acid ester compounds as products were obtained, and the yield and the isomer ratio of the dicarboxylic acid ester compounds were calculated by an internal reference method using the following expression.

{Yield of dicarboxylic acid ester compound(mol %)}={Total acquisition mass of dicarboxylic acid ester compound/256.3}/{Raw material feed mass/136.2}×100

{Isomer ratio(%)}={Methyl-4-(1-methoxy-2-methyl-1-oxopropan-2-yl)-1-methylcyclohexane carboxylate(GC %)}/{Total of dicarboxylic acid ester compounds(GC %)}×100

The isomer in the description means a structural isomer having a carbonyl group at a different insertion position.

[GC-MS]

As GC-MS measurement apparatus, a GC-MS spectrometer POLARIS Q made by Thermo ELECTRON Corporation was used.

[NMR]

NMR was measured under the following conditions.
Apparatus: Bruker Avance 600II (600 MHz-NMR)
Mode: Proton, Carbon, DEPT 45°, 90°, and 135°, Carbon i.g., and INADEQUATE, HSQC, H2BC, HMBC
Solvent: CDCl3 (deuterated chloroform)
Internal reference substance: tetramethylsilane Example 1

Manufacturing of methyl-4-(1-methoxy-2-methyl-1-oxopropan-2-yl)-1-methylcyclohexane carboxylate

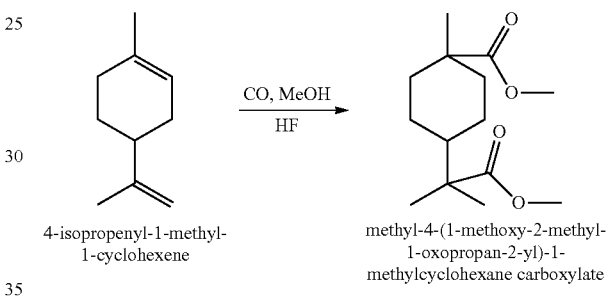

4-isopropenyl-1-methyl-1-cyclohexene methyl-4-(1-methoxy-2-methyl-1-oxopropan-2-yl)-1-methylcyclohexane carboxylate

[Carbonylation step]

Using a stainless steel autoclave with an internal volume of 500 ml including a Nack drive type stirrer and three inlet nozzles at the top and one extraction nozzle at the bottom, with a jacket for internal temperature control, the carbonylation step was performed as follows.

First, the atmosphere in the autoclave was substituted with carbon monoxide. Subsequently, 230 g (11.5 mol) of anhydrous hydrogen fluoride was introduced into the autoclave, and the liquid temperature in the autoclave was set to −27° C. The inside of the autoclave was then pressurized to 2 MPa with carbon monoxide.

In the autoclave with the reaction temperature being kept at −27° C., and the reaction pressure being kept at 2 MPa, 104.4 g (0.77 mol) of 4-isopropenyl-1-methyl-1-cyclohexene was supplied from the top of the autoclave, so that the carbonylation reaction was performed. After completion of the supply, with stirring of the reaction liquid being continued for about 10 minutes until no absorption of carbon monoxide was observed, an alicyclic dicarboxylic acid fluoride was thereby obtained.

[Esterification Step]

Subsequently, in the autoclave with the reaction temperature being kept at −27° C., 49.1 g (1.53 mol) of methanol was supplied from the top of the autoclave, so that esterification of the alicyclic dicarboxylic acid fluoride was performed with the reaction liquid being stirred for 1 hour.

The reaction liquid was extracted from the bottom of the autoclave into ice water, so that an oil phase and an aqueous phase were separated. Subsequently, the oil phase was washed twice with 100 ml of 2% caustic soda aqueous solution and twice with 100 ml of distilled water, and was dehydrated with 10 g of anhydrous sodium sulfate. After dehydration, the produced liquid was analyzed by gas chromatography. As a result, the yield of the dicarboxylic acid ester compound was 26.6 mol % (on 4-isopropenyl-1-methyl-1-cyclohexene basis), and the yield of methyl-4-(1-methoxy-2-methyl-1-oxopropan-2-yl)-1-methylcyclohexane carboxylate was 21.1 mol % (on 4-isopropenyl-1-methyl-1-cyclohexene basis, isomer ratio: 79.2%).

[Isolation and Refining of Product]

By reduced-pressure distillation of the liquid produced in the esterification step with an evaporator, low-boiling point substances were removed from the liquid. Subsequently, the low-boiling point substance-removed liquid was rectified using a rectification column with a theoretical plate number of 20 (distillation temperature: 177° C., degree of vacuum: 20 torr). Through the rectification, 42.0 g of a product as main fraction having an isomer ratio of 92.0% by gas chromatography analysis (distilled yield: 93.2 mol %, on methyl-4-(1-methoxy-2-methyl-1-oxopropan-2-yl)-1-methylcyclohexane carboxylate basis) was obtained.

<Product Identification>

As a result of GC-MS analysis, the product obtained in the isolation and refining in Example 1 had a molecular weight of 256.

Using the NMR apparatus, 1H-NMR measurement, 13C-NMR measurement, DEPT 45°, 90°, and 135°-NMR measurement, Carbon i.g.-NMR measurement, INADEQUATE-NMR measurement, HSQC-NMR measurement, H2BC-NMR measurement, and HMBC-NMR measurement were performed. The results of 1H-NMR measurement and 13C-NMR measurement are shown as follows, and the results of DEPT 45°, 90°, and 135°-NMR measurement, Carbon i.g.-NMR measurement, INADEQUATE-NMR measurement, HSQC-NMR measurement, H2BC-NMR measurement, and HMBC-NMR measurement are shown in FIGS. 1 to 10.

[NMR Measurement Results of Product Obtained in Example 1]

1H-NMR (600 MHz, CDCl3, TMS, ppm) δ: 0.994-1.055 (m, 14H), 1.380-1.401 (m, 2H), 1.488 (m, 1H), 2.147-2.168 (m, 2H), 3.567 (s, 3H), 3.596 (s, 3H)

13C-NMR (600 MHz, CDCl3, TMS, ppm) δ: 21.74, 24.75, 28.01, 35.85, 43.25, 44.46, 45.17, 51.33, 51.41, 177.31, 178.34

Figure 2:
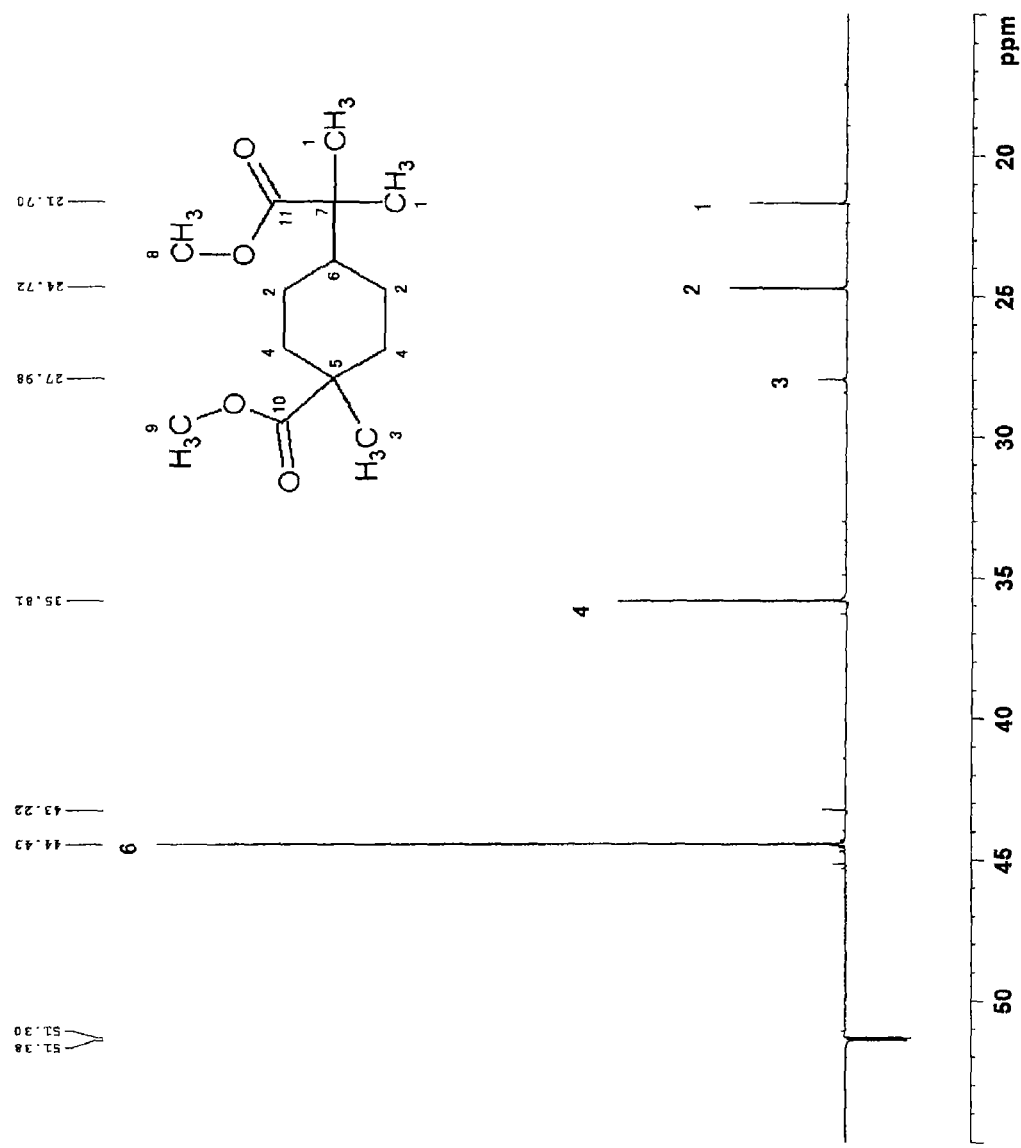
FIG. 2 is a chart showing DEPT 90°-NMR measurement results of a product obtained in Example 1.
Figure 3:
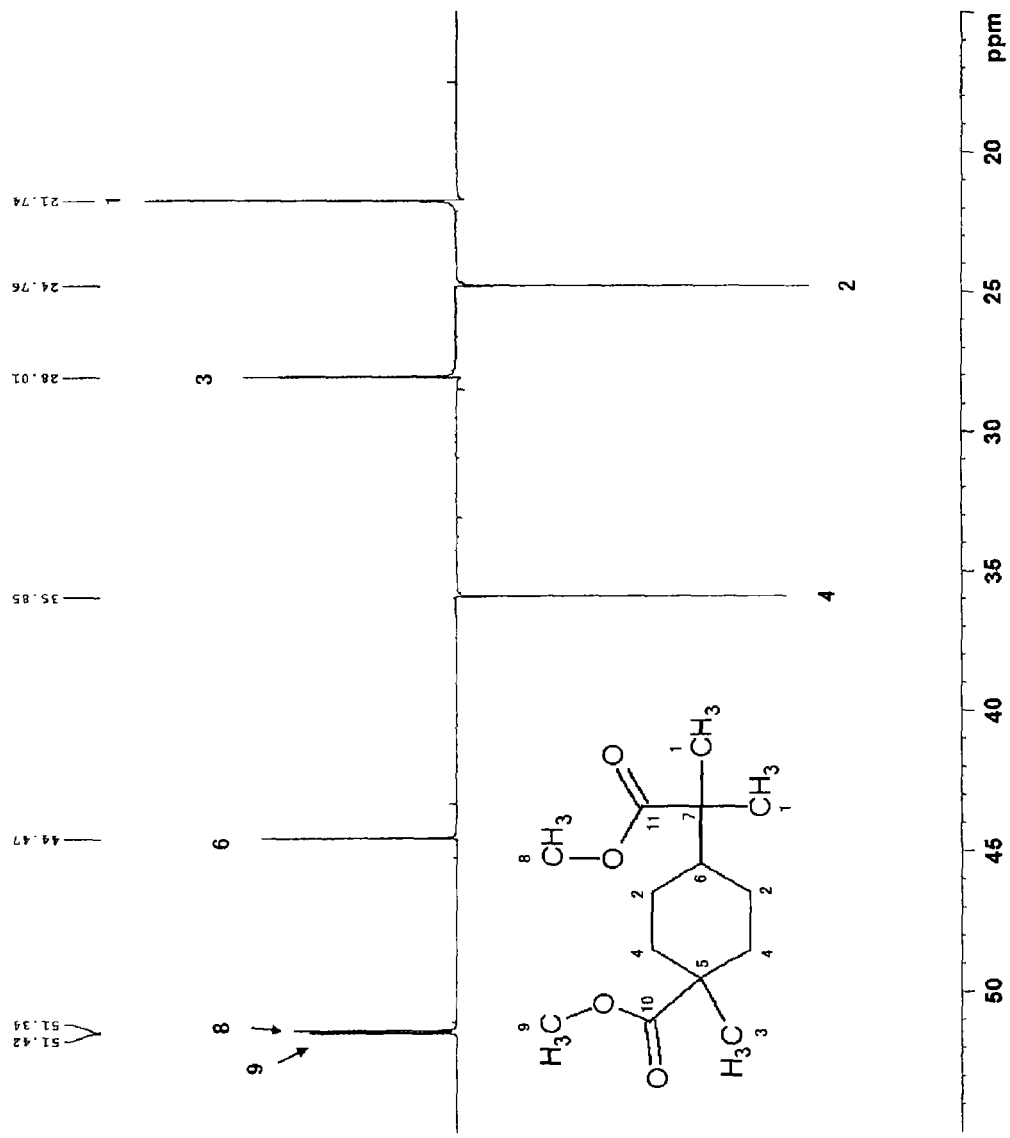
FIG. 3 is a chart showing DEPT 135°-NMR measurement results of a product obtained in Example 1.
Figure 4:
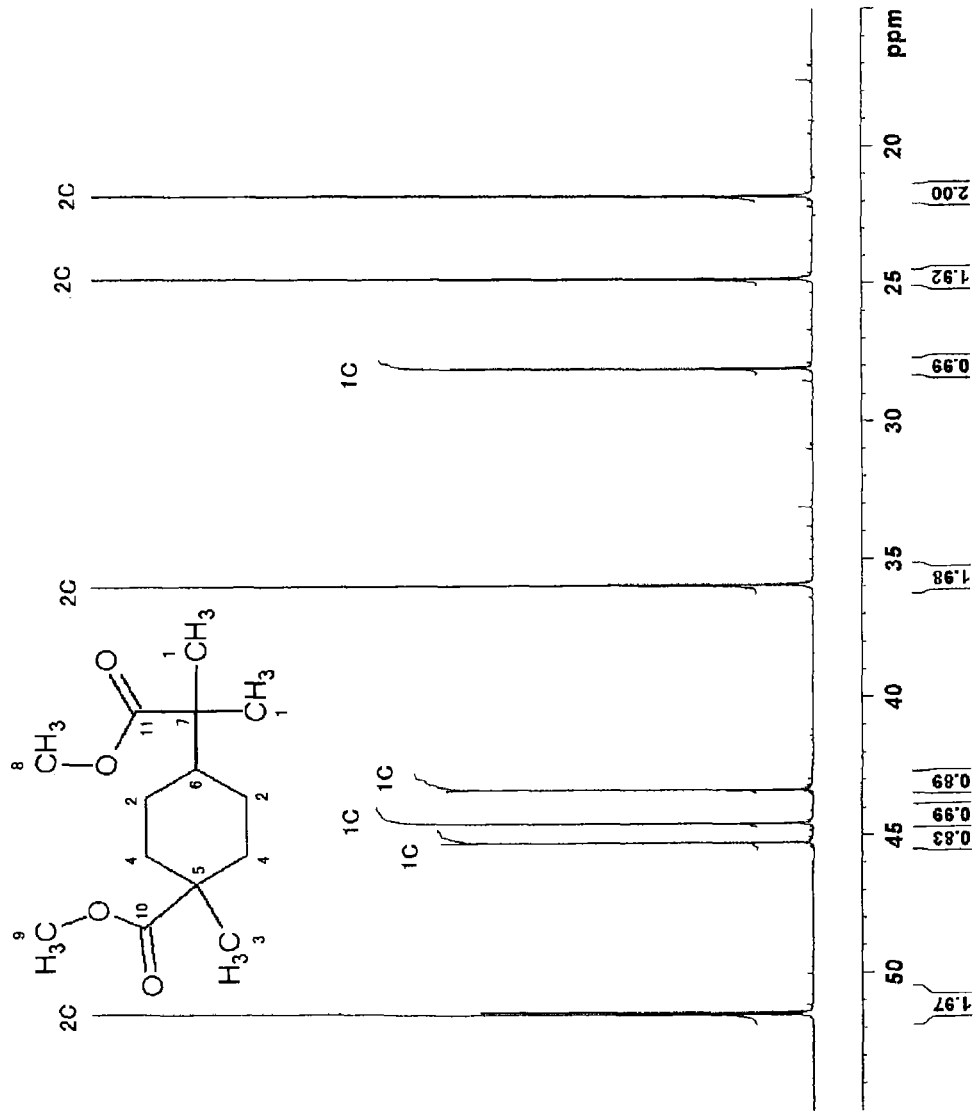
FIG. 4 is a chart showing Carbon i.g.-NMR measurement results of a product obtained in Example 1.
Figure 5:
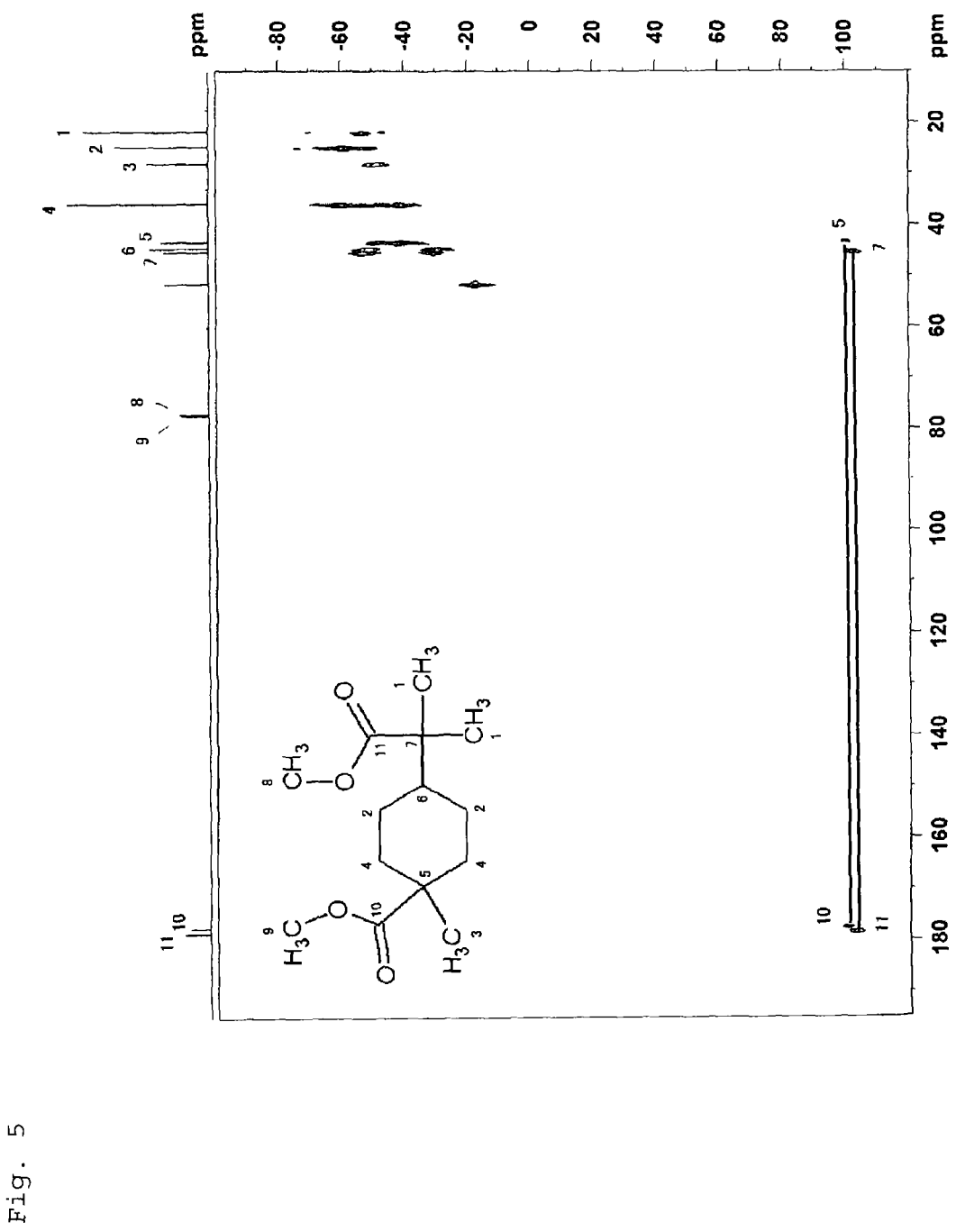
FIG. 5 is a chart showing INADEQUATE-NMR measurement results of a product obtained in Example 1.
Figure 6:
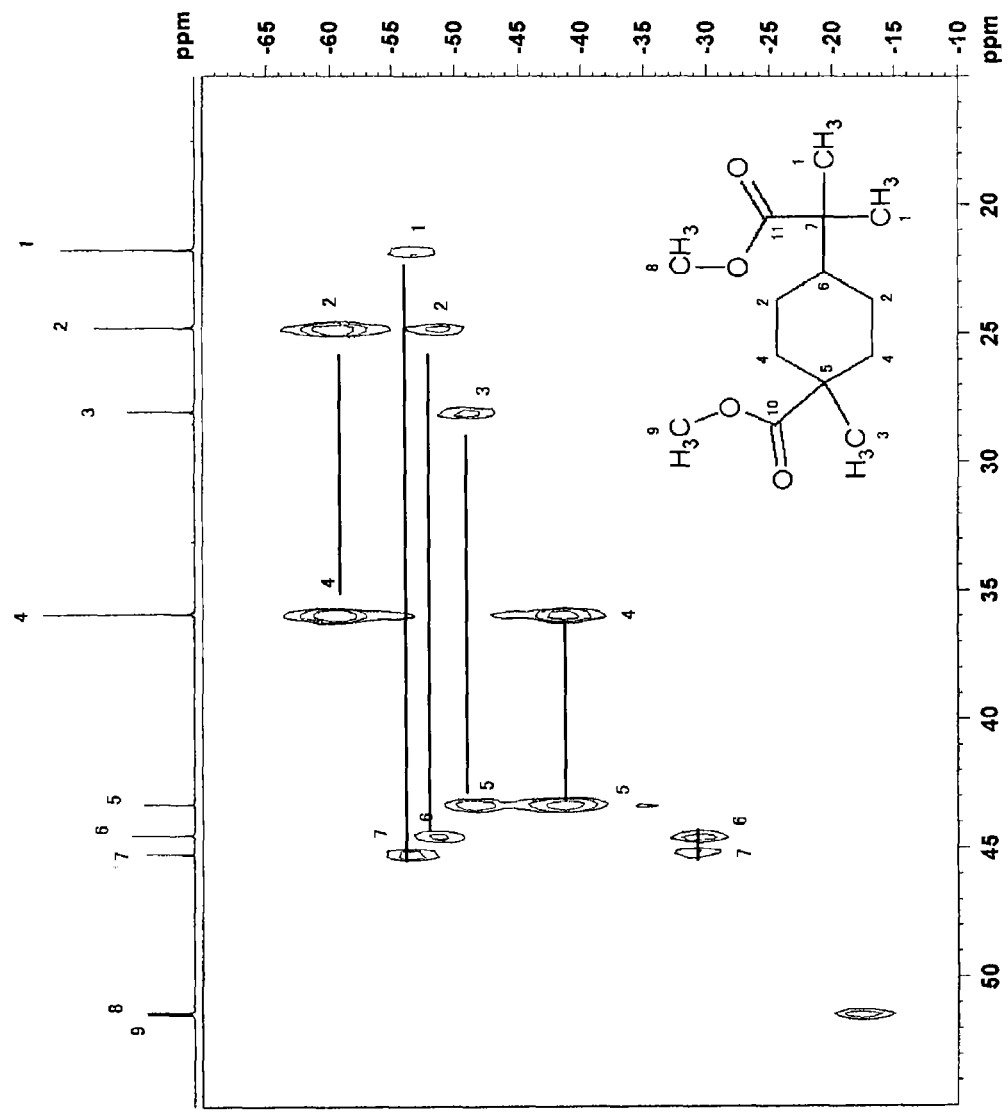
FIG. 6 is an enlarged chart showing measurement results in a portion from 15 to 55 ppm in FIG. 5.
Figure 7:
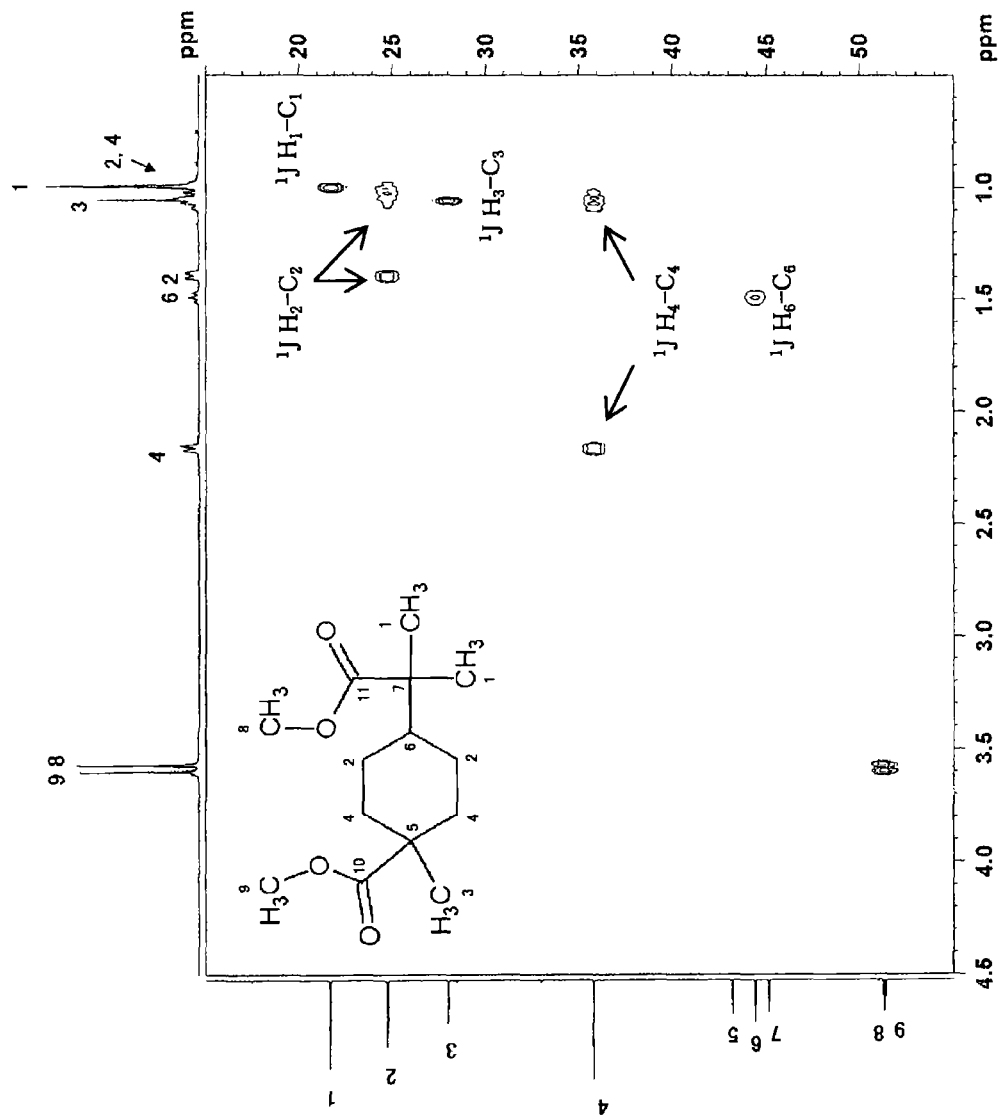
FIG. 7 is a chart showing HSQC-NMR measurement results of a product obtained in Example 1.
Figure 8:
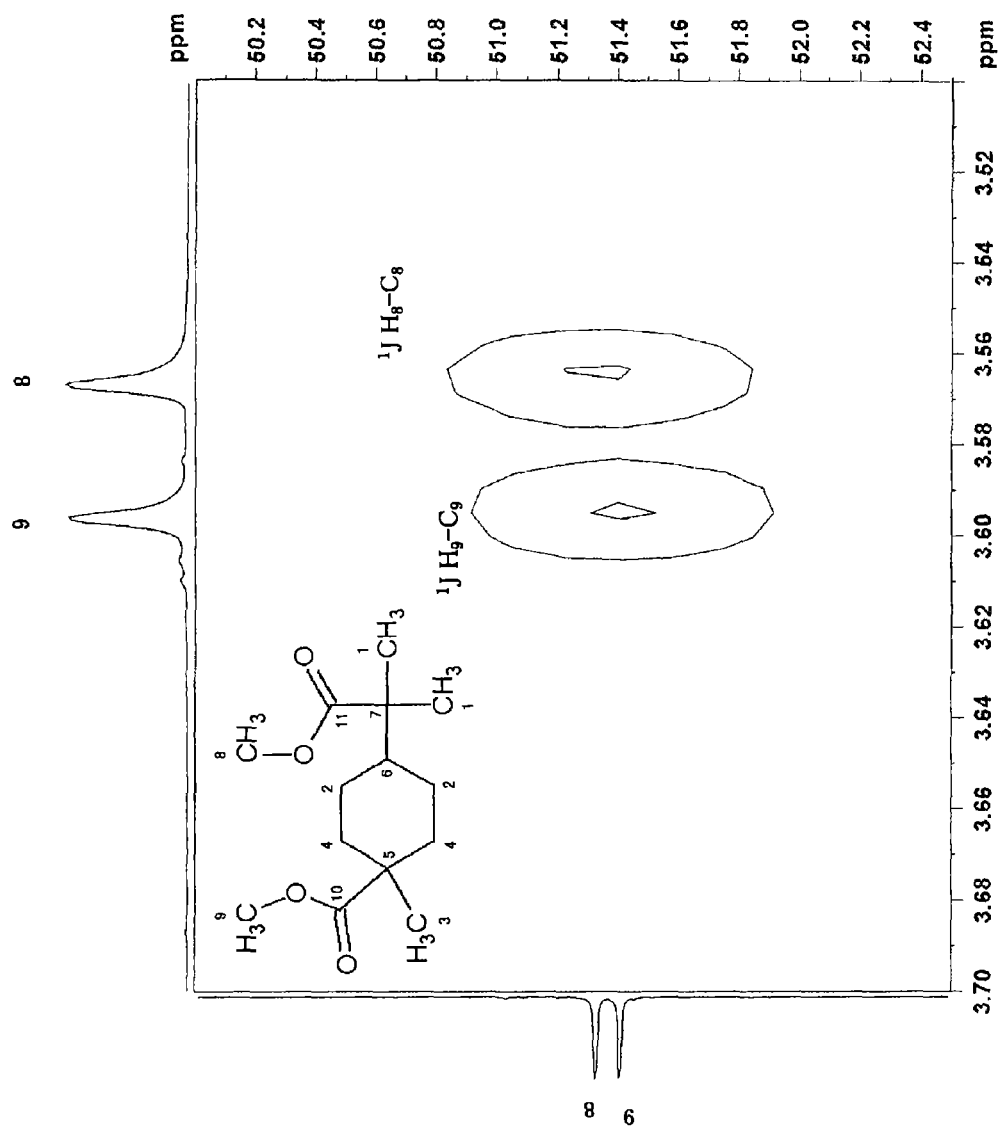
FIG. 8 is an enlarged chart showing measurement results in a portion from 3.50 to 3.70 ppm in FIG. 7.
Figure 9:
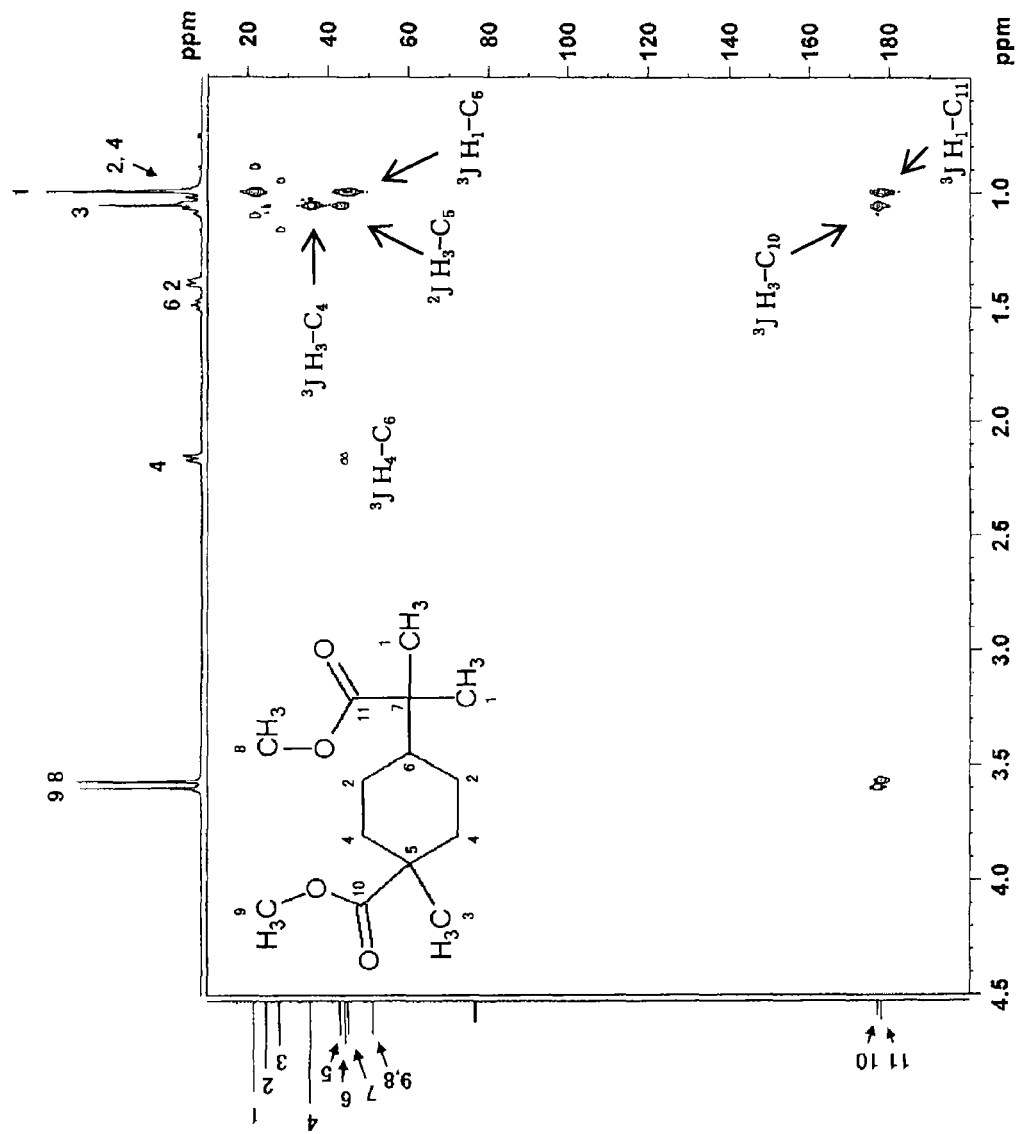
FIG. 9 is a chart showing HMBC-NMR measurement results of a product obtained in Example 1.
Figure 10:
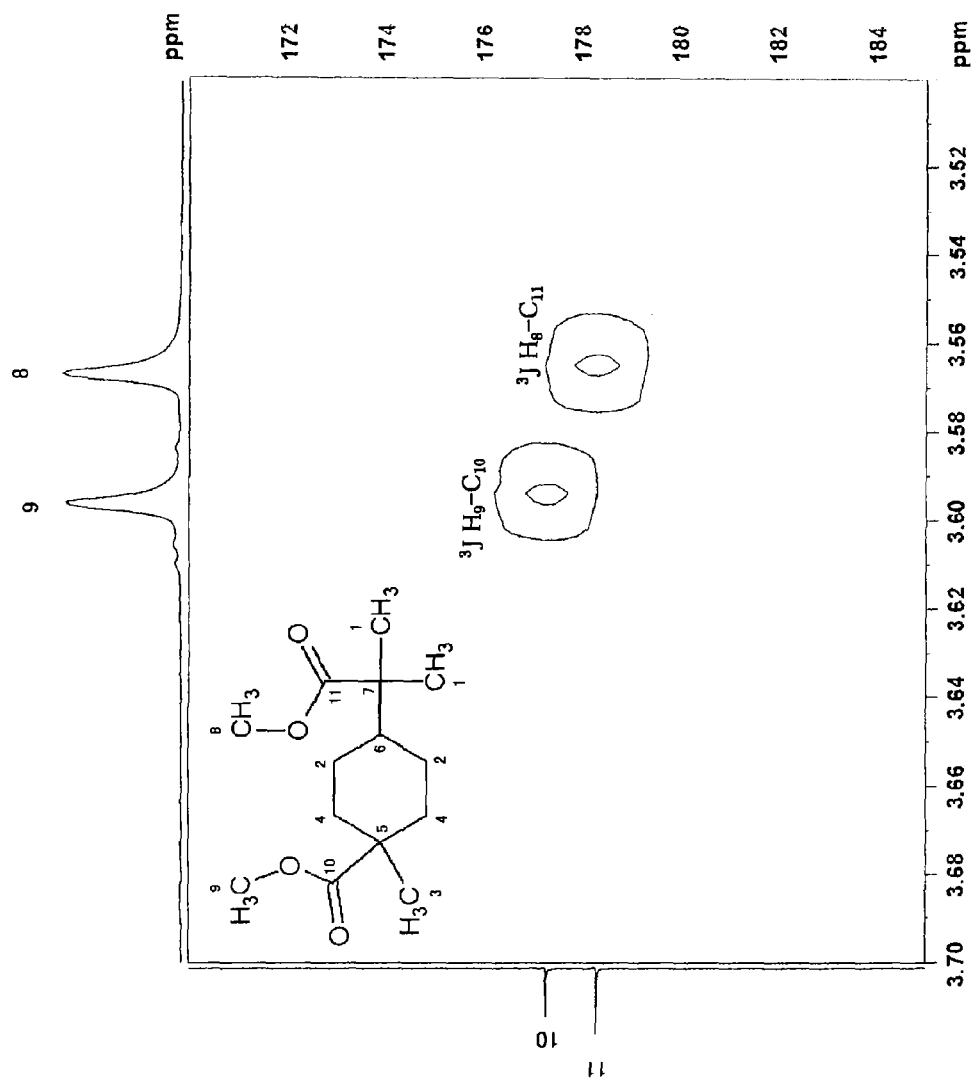
FIG. 10 is an enlarged chart showing measurement results in a portion from 3.50 to 3.70 ppm in FIG. 9.

FIG. 1 is a chart showing DEPT 45°-NMR measurement results. From FIG. 1, it was found that the fifth and seventh peaks for quaternary carbon atoms were missing. FIG. 2 is a chart showing DEPT 90°-NMR measurement results. From FIG. 2, it was found that the sixth peak for a tertiary carbon atom was strongly detected. FIG. 3 is a chart showing DEPT 135°-NMR measurement results. From FIG. 3, it was found that the second and fourth peaks for secondary carbon atoms were detected in the downward direction. FIG. 4 is a chart showing Carbon i.g.-NMR measurement results. From FIG. 4, the number of carbon was confirmed. FIG. 5 and FIG. 6 are charts showing INADEQUATE-NMR measurement results (FIG. 6 is an enlarged chart showing measurement results in a portion for 15 to 55 ppm in FIG. 5.). From FIG. 5 and FIG. 6, the correlations of direct bonding between carbons were elucidated. FIG. 7 and FIG. 8 are charts showing HSQC-NMR measurement results (FIG. 8 is an enlarged chart showing measurement results in a portion from 3.50 to 3.70 ppm in FIG. 7.). From FIG. 7 and FIG. 8, the hydrogen atom bonded to each carbon atom was determined. FIG. 9 and FIG. 10 are charts showing HMBC-NMR measurement results (FIG. 10 is an enlarged chart showing measurement results in a portion from 3.50 to 3.70 ppm in FIG. 9.). From FIG. 9 and FIG. 10, a hydrogen atom which positions 2 bonds away from each carbon atom was determined.

Based on comprehensive determination from the measurement results, the main component of the product obtained in Example 1 was identified to be methyl-4-(1-methoxy-2-methyl-1-oxopropan-2-yl)-1-methylcyclohexane carboxylate.

<Identification of Steric Structure>

The steric structure of methyl-4-(1-methoxy-2-methyl-1-oxopropan-2-yl)-1-methylcyclohexane carboxylate obtained in Example 1 was identified as follows by NMR measurement.

Figure 11:
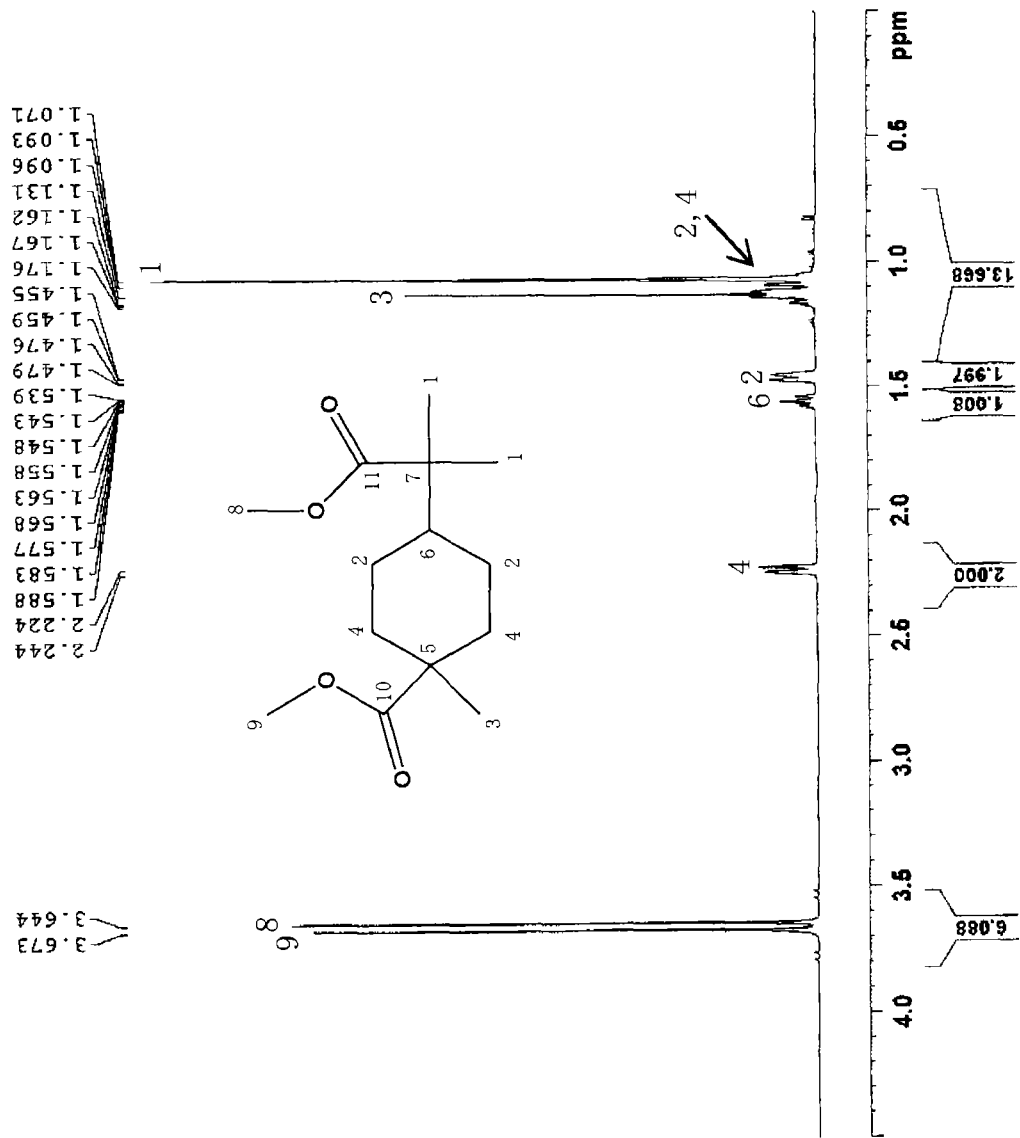
FIG. 11 is a chart showing 1H-NMR measurement results of a product obtained in Example 1.
Figure 12:
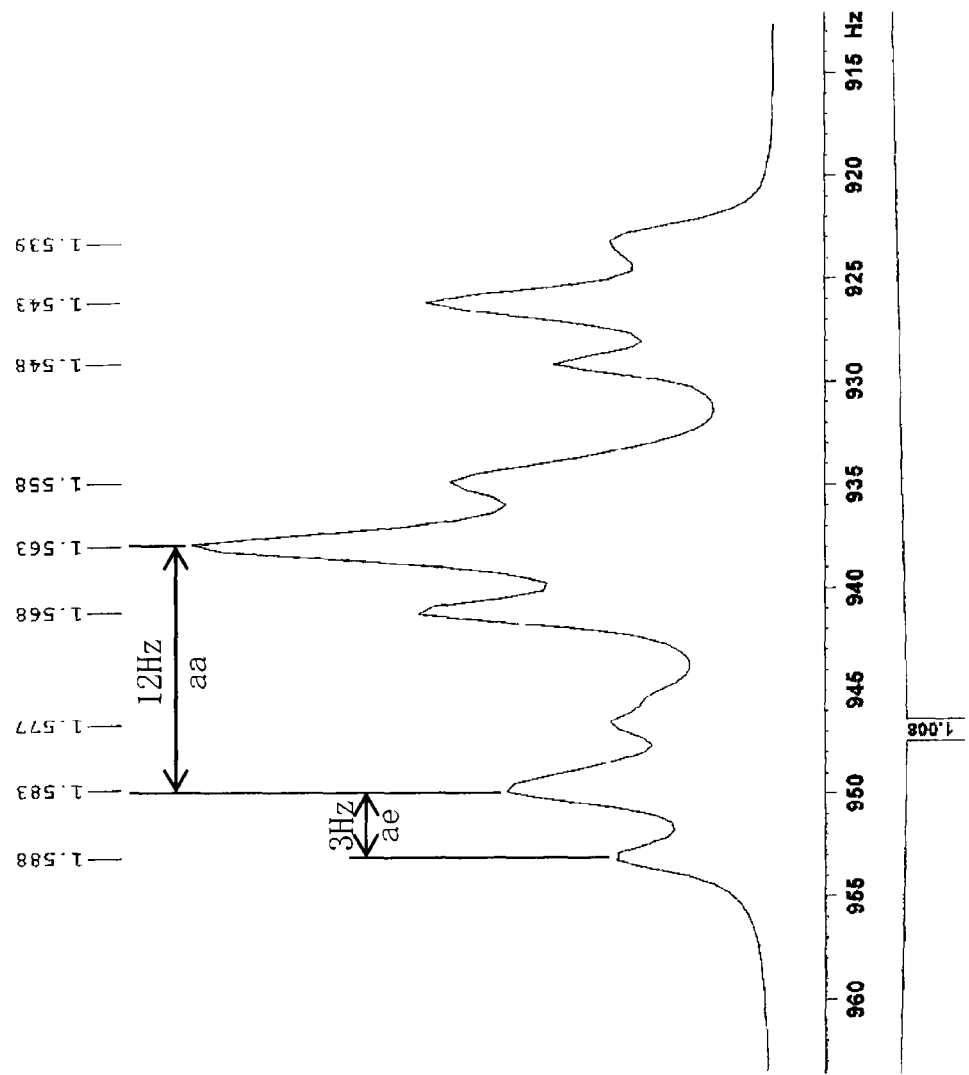
FIG. 12 is an enlarged chart expressing the horizontal axis of a peak 6 of FIG. 1 in Hz.

FIG. 11 is a chart showing 1H-NMR measurement results. FIG. 12 is an enlarged chart of a peak 6 (peak of a hydrogen atom bonded to the carbon to which a 1-methoxy-2-methyl-1-oxopropan-2-yl group is bonded) of FIG. 11. From FIG. 12, it was shown that the peak was split into 9 and the binding constant of each peak was 12 Hz or 3 Hz. From this, it was shown that the hydrogen atom at a position 6 (hydrogen atom bonded to the carbon to which a 1-methoxy-2-methyl-1-oxopropan-2-yl group is bonded) of the compound shown in FIG. 11 (methyl-4-(1-methoxy-2-methyl-1-oxopropan-2-yl)-1-methylcyclohexane carboxylate) was at the axial position of a cyclohexane ring.

Figure 13:
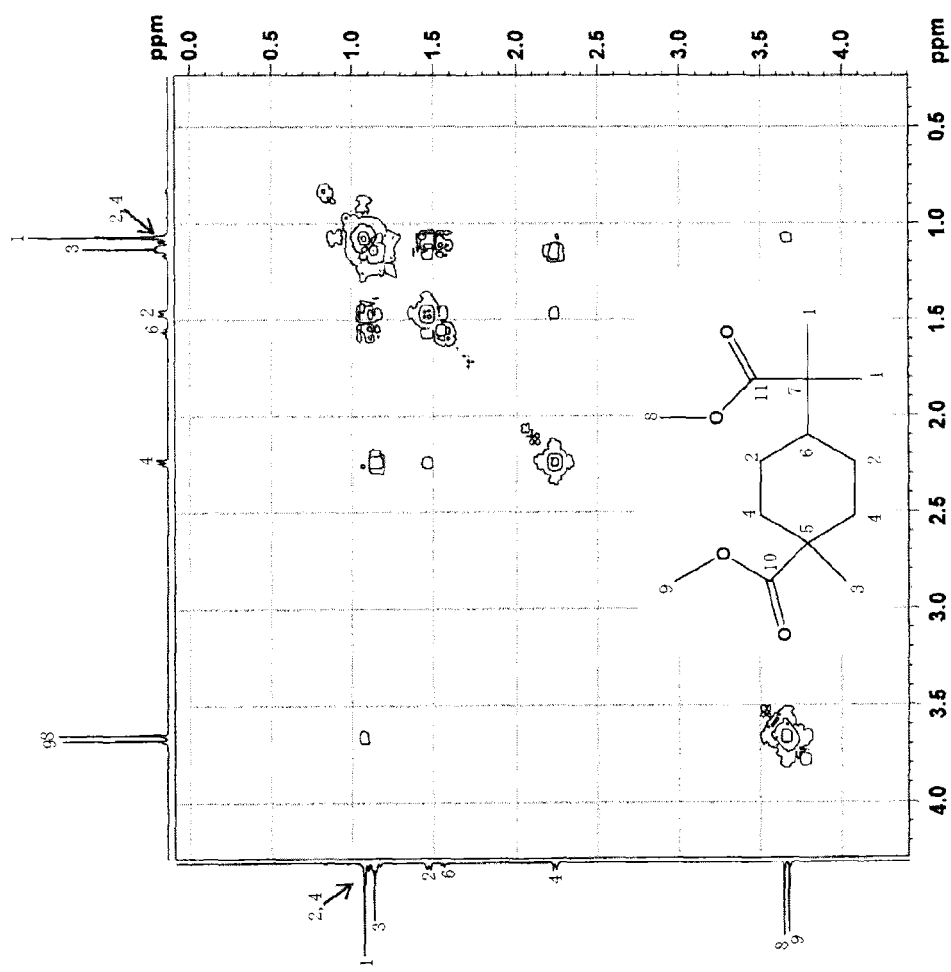
FIG. 13 is a chart showing COZY-NMR measurement results of a product obtained in Example 1.
Figure 14:
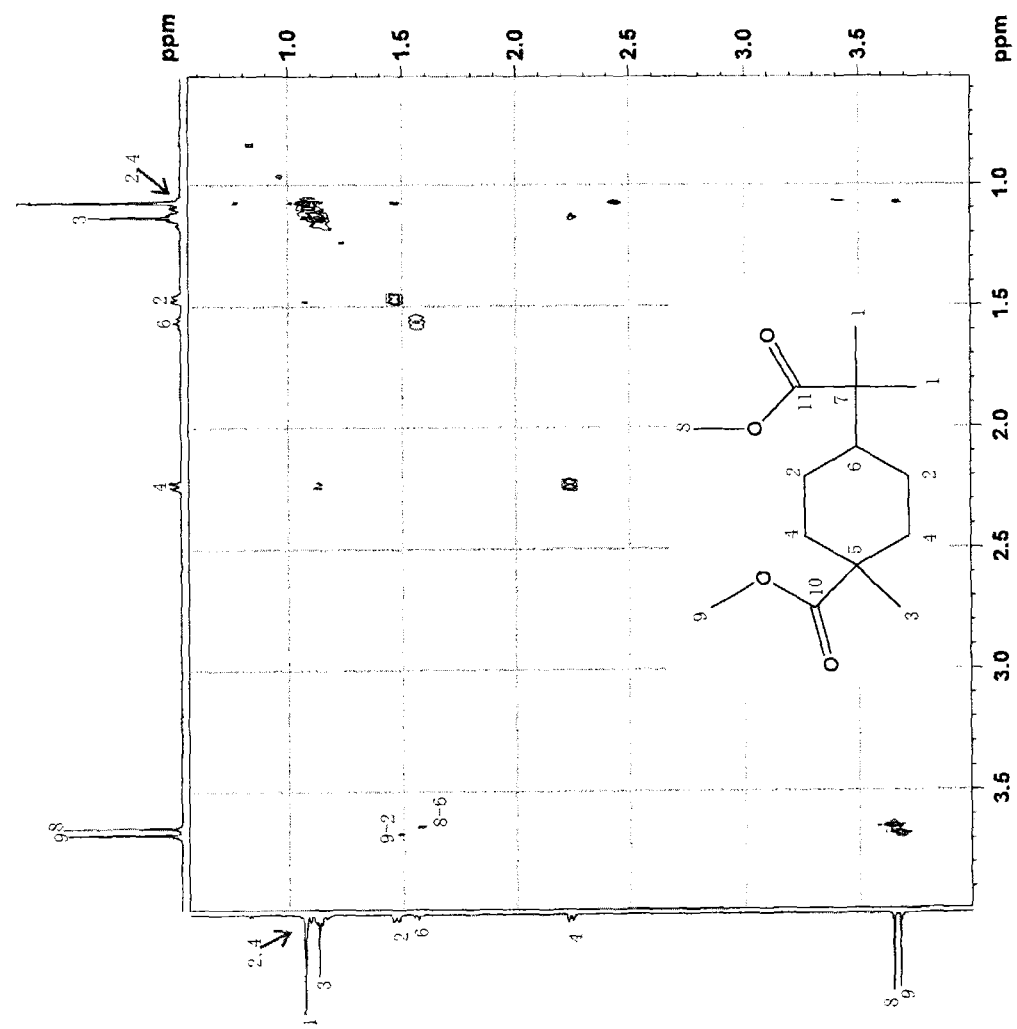
FIG. 14 is a chart showing NOEZY-NMR measurement results of a product obtained in Example 1.

FIG. 13 is a chart showing COZY-NMR measurement results. FIG. 14 is a chart showing NOEZY-NMR measurement results. From the comparison of the measurement results in FIG. 13 and FIG. 14, it was shown that correlations specific to NOEZY-NMR measurement exist between the hydrogen atoms at position 2 and position 9 and between the hydrogen atoms at position 6 and position 8 of the compound shown in FIGS. 13 and 14 (methyl-4-(1-methoxy-2-methyl-1-oxopropan-2-yl)-1-methylcyclohexane carboxylate). In other words, it was shown that the hydrogen atoms at position 2 and position 9 were spatially located at a close distance, and the hydrogen atoms at position 6 and position 8 were spatially located at a close distance. From this, it was shown that the compound shown in FIGS. 13 and 14 (methyl-4-(1-methoxy-2-methyl-1-oxopropan-2-yl)-1-methylcyclohexane carboxylate) has a carboxylate group at the equatorial position of a cyclohexane ring.

From the measurement results described above, the steric structure of methyl-4-(1-methoxy-2-methyl-1-oxopropan-2-yl)-1-methylcyclohexane carboxylate obtained in Example 1 was identified to be a trans configuration represented by the following formula (1-1a).

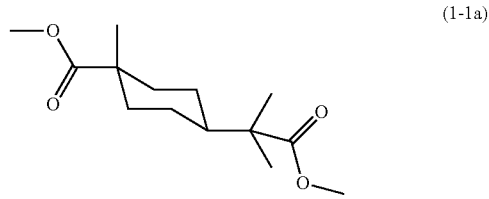

(1-1a)

Example 2

Except that the reaction temperature in a carbonylation step was set to −15° C., the carbonylation step, an esterification step, and isolation and refining of a product were performed in the same way as in Example 1. After isolation and refining, the produced liquid was analyzed by gas chromatography. As a result, the yield of the dicarboxylic acid ester compound was 25.6 mol % (on 4-isopropenyl-1-methyl-1- cyclohexene basis), and the yield of methyl-4-(1-methoxy-2-methyl-1-oxopropan-2-yl)-1-methylcyclohexane carboxylate was 18.7 mol % (on 4-isopropenyl-1-methyl-1-cyclohexene basis, isomer ratio: 73.0%).

Example 3

Except that the carbon monoxide pressure in autoclave was set to 3 MPa, a carbonylation step, an esterification step, and isolation and refining of a product were performed in the same way as in Example 2. After isolation and refining, the produced liquid was analyzed by gas chromatography. As a result, the yield of the dicarboxylic acid ester compound was 27.5 mol % (on 4-isopropenyl-1-methyl-1-cyclohexene basis), and the yield of methyl-4-(1-methoxy-2-methyl-1-oxopropan-2-yl)-1-methylcyclohexane carboxylate was 20.1 mol % (on 4-isopropenyl-1-methyl-1-cyclohexene basis, isomer ratio: 73.1%).

INDUSTRIAL APPLICABILITY

The new alicyclic dicarboxylic acid ester compound obtained in the present invention is useful as various industrial chemical raw materials and raw materials for manufacturing functional optical materials and functional electronic materials.

The invention claimed is:

1. An alicyclic dicarboxylic acid ester compound represented by the following formula (1):

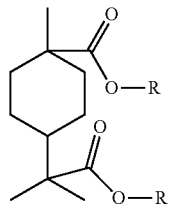

(1)

wherein R each independently represent an alkyl group having 1 to 4 carbon atoms.

2. The alicyclic dicarboxylic acid ester compound according to claim 1, wherein the compound has a steric structure represented by the following formula (1-1):

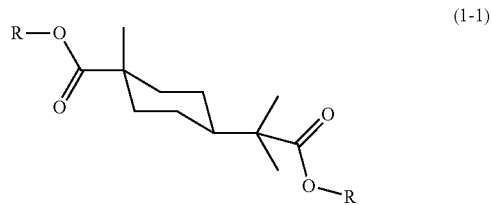

(1-1)

wherein R each independently represent an alkyl group having 1 to 4 carbon atoms.

3. A method of manufacturing an alicyclic dicarboxylic acid ester compound comprising the steps of:
reacting 4-isopropenyl-1-methyl-1-cyclohexene represented by the following formula (3) with carbon monoxide in the presence of hydrogen fluoride so as to produce an alicyclic dicarboxylic acid fluoride represented by the following formula (2); and
reacting the produced alicyclic dicarboxylic acid fluoride represented by the following formula (2) with alcohol so as to produce an alicyclic dicarboxylic acid ester compound represented by the following formula (1):

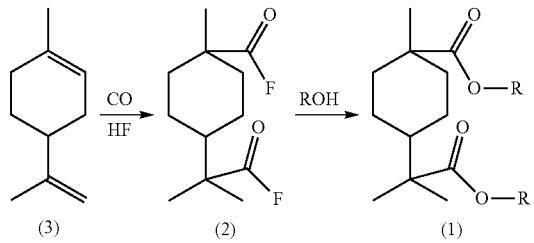

wherein R each independently represent an alkyl group having 1 to 4 carbon atoms.

* * * * *